(12) United States Patent
He et al.

(10) Patent No.: US 10,648,891 B2
(45) Date of Patent: May 12, 2020

(54) EVALUATING BLACK POWDER FORMATION OF HYDROCARBON GAS FLOWED THROUGH PIPELINES

(71) Applicant: Saudi Arabian Oil Company, Dhahran (SA)

(72) Inventors: Yufeng He, Al-Khobar (SA); Rohit Patwardhan, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 682 days.

(21) Appl. No.: 15/452,321

(22) Filed: Mar. 7, 2017

(65) Prior Publication Data

US 2018/0259426 A1   Sep. 13, 2018

(51) Int. Cl.
| | |
|---|---|
| *G01M 99/00* | (2011.01) |
| *G01N 15/08* | (2006.01) |
| *G01N 33/00* | (2006.01) |
| *G06Q 10/00* | (2012.01) |
| *G06Q 50/06* | (2012.01) |
| *G01N 17/00* | (2006.01) |

(Continued)

(52) U.S. Cl.
CPC ...... *G01M 99/008* (2013.01); *G01N 15/0806* (2013.01); *G01N 17/00* (2013.01); *G01N 33/0036* (2013.01); *G06Q 10/20* (2013.01); *G06Q 50/06* (2013.01); *C10L 3/106* (2013.01); *G01N 33/225* (2013.01); *G01N 2015/084* (2013.01)

(58) Field of Classification Search
CPC . G01M 99/008; G01N 15/0806; G01N 17/00; G01N 2015/084
See application file for complete search history.

(56) References Cited

U.S. PATENT DOCUMENTS

| | | |
|---|---|---|
| 3,014,082 A | 12/1961 | Woertz |
| 2009/0211335 A1 | 8/2009 | Jovancicevic et al. |

(Continued)

FOREIGN PATENT DOCUMENTS

WO   2016027235   2/2016

OTHER PUBLICATIONS

A. Dugstad et al., Experimental Study of Black Powder Formation in Field TEG solutions, Jan. 1, 2011, Nace International Corrosion Conference and Expo, XPO55478154, pp. 12 (Year: 2011).*

(Continued)

*Primary Examiner* — Manuel A Rivera Vargas
*Assistant Examiner* — Yaritza H Perez Bermudez
(74) *Attorney, Agent, or Firm* — Fish & Richardson P.C.

(57) ABSTRACT

Sales gas output from a glycol dehydration unit in a gas plant is flown into a sales gas pipeline. One or more operational parameters of the glycol dehydration unit are received. One or both of an amount of glycol carryover and an amount of water carryover in sales gas output from the glycol dehydration unit in the gas plant are determined based on the one or more operational parameters of the glycol dehydration unit. An amount of glycol and water co-condensation in the sales gas pipeline is determined based on one or more operational parameters of the sales gas pipeline and the one or both of the amount of glycol carryover and the amount of water carryover. An amount of black powder formation of the sales gas is determined based on the amount of glycol and water co-condensation.

20 Claims, 6 Drawing Sheets

(51) Int. Cl.
   *G01N 33/22* (2006.01)
   *C10L 3/10* (2006.01)

(56) References Cited

U.S. PATENT DOCUMENTS

2015/0343416 A1* 12/2015 Fadhel .................. B01J 8/0055
                                                    252/186.1
2016/0354790 A1* 12/2016 Hassell .................. C10L 3/101

OTHER PUBLICATIONS

Gulf Cooperation Council Examination issued in GCC Application No. GC 2018-34884 on Sep. 17, 2019, 3 pages.
Dugstad and Sirnes, "Experimental Study of Black Powder Formation in Field Teg Solutions," XPO55478154, Nace International Corrosion Conference and Expo, Jan. 1, 2011, 12 pages.
Khan et al., "Review of black powder in gas pipelines—an industrial perspective," XPO29175907Journal of Natural Gas Science and Engineering, vol. 25, May 15, 2015, 11 pages.
International Search Report and Written Opinion issued in International Application No. PCT/US2018/020106 dated Jun. 6, 2018, 15 pages.
Li Yan; "Evaluation of the Corrosiveness of Glycol-Water Mixtures in Dry Gas Transmission Lines", NOVA Research & Technology Corporation, Catalog No. PR-261-123602-R01, Mar. 29, 2013, 28 pages.
Sherik et al.; Effect of Triethylene Glycol on Corrosion of Carbon Steel in H2S, CO2, and O2 Environments:, NACE International, Corrosion Conference and Expo-2010, Paper No. 10188, 11 pages.
John Smart III and Randy Roberts: "Possible Glycol Corrosion in Nominally Dry Gas Pipelines", NACE International, Corrosion NACExpo 2006, 61st Annual Conference and Exposition, Paper No. 06442,15 pages.
Baker, Pipeline Corrosion—Final Report, Submitted to the US Dept. of Transportation Pipeline and Hazardous Materials Safety Administration Office of Pipeline Safety, Nov. 2008, 78 pages.
H. Kordabadi et al.; "Manage TEG liquid and corrosion in sales gas pipelines", internet: http://www.gasprocessingnews.com/features/201310/manage-teg-liquid-and-corrosion-in-sales-gas-pipelines.aspx; 8 pages.
John S. Smart; "Black Powder in Gas Pipelines", presented to the 2014 Texas Gas Association Conference, San Marcos, TX, Nov. 13, 2014, 28 pages.
Olivier Trifilieff et al.; "Black Power Removal from Transmission Pipelines: Diagnostics and Solutions", PALL, Fuels and Chemicals, Scientific & Technical Report, Bahrain, Jan. 19-21, 2009.

* cited by examiner

EVALUATING BLACK POWDER FORMATION OF HYDROCARBON GAS FLOWED THROUGH PIPELINES

TECHNICAL FIELD

This disclosure relates to evaluating black powder formation of hydrocarbon gas flowed through pipelines.

BACKGROUND

"Black powder" refers to blackish material such as solids or solid deposits that collects in gas pipelines. In some implementations, the black powder has a wet, tar-like appearance, or may appear as a dry, fine powder material composed of iron hydroxide, iron carbonate, iron sulfide, or other components and may be mixed with various contaminants such as salts, sand, and liquid hydrocarbons.

Deposition or formation of black powder can occur if there are solids in the pipeline fluid and the velocity of the gas flow is not high enough to drag the particles along by viscous flow forces. Sediment deposits can lead to blockage of the line, especially during pigging, while flowing powder can damage compressors, plug filters, and damage user equipment. Black powder also represents a threat to natural gas's reputation as a clean fuel.

SUMMARY

This disclosure relates to evaluating black powder formation of hydrocarbon gas flowed through pipelines (for example, sales gas), including modeling and predicting black powder formation in sales gas transmitted in gas pipelines.

A system includes a sales gas pipeline coupled to a glycol dehydration unit in a gas plant and operable to receive sales gas output from the gas plant; and a computer system. The computer system is operable to receive one or more operational parameters of the glycol dehydration unit in the gas plant; determine an amount of glycol carryover and an amount of water carryover in the sales gas output from the glycol dehydration unit, based on the one or more operational parameters of the glycol dehydration unit; determine an amount of glycol and water co-condensation in the sales gas pipeline based on the amount of glycol carryover, the amount of water carryover, and one or more operational parameters of the sales gas pipeline; and determine an amount of black powder formation of the sales gas in the sales gas pipeline based on the amount of glycol and water co-condensation.

In some implementations, the system further includes the gas plant that includes the glycol dehydration unit.

In some implementations, the system further includes one or more sensors for measuring the one or more operational parameters of the glycol dehydration unit, wherein the one or more operational parameters of the glycol dehydration unit include one or more of: a flowrate of wet gas that is input into the glycol dehydration unit, temperature of the of wet gas that is input into the glycol dehydration unit, glycol circulation rate, or contactor pressure.

In some implementations, the one or more operational parameters of the glycol dehydration unit are measured over time; and the computer system is operable to receive one or more operational parameters of the glycol dehydration unit over the time.

In some implementations, the system further includes one or more sensors for measuring the one or more operational parameters of the sales gas pipeline, wherein the one or more operational parameters of the sales gas pipeline include one or more of pressure or temperature of the sales gas pipeline or ambient temperature.

In some implementations, the system further includes one or more sensors for measuring at least one operating condition of the glycol dehydration unit, wherein the computer system is operable to execute a model of glycol carryover as a function of the one or more operational parameters of the glycol dehydration unit, the model of glycol carryover matching the at least one operating condition of the glycol dehydration unit.

In some implementations, the system further includes one or more sensors for measuring at least one operating condition of the glycol dehydration unit, wherein the computer system is operable to execute a model of water carryover as a function of the one or more operational parameters of the glycol dehydration unit, the model of water carryover matching at least one operating condition of the glycol dehydration unit.

In some implementations, the computer system is operable to determine the amount of glycol and water co-condensation in the sales gas pipeline based on a model of the glycol and water co-condensation, the model of the glycol and water co-condensation including a function of the one or more operational parameters of the sales gas pipeline.

In some implementations, the system further includes a filter station downstream to the sales gas pipeline and configured to filter black powder formation of the sales gas; wherein the computer system is operable to receive a measurement at the filter station of the black powder formation of the sales gas; and determine the amount of black powder formation of the sales gas based on a model of black powder formation, the model of black powder formation including a function of the amount of glycol and water co-condensation, the model of black powder formation matching the measurement of the black powder formation of the sales gas at the filter station.

In some aspects, a method includes flowing sales gas output from a glycol dehydration unit in a gas plant into a sales gas pipeline; receiving, by operation of data processing apparatus, one or more operational parameters of the glycol dehydration unit in the gas plant; determining, by operation of the data processing apparatus, one or both of an amount of glycol carryover and an amount of water carryover in sales gas output from the glycol dehydration unit in the gas plant based on the one or more operational parameters of the glycol dehydration unit; determining, by operation of the data processing apparatus, an amount of glycol and water co-condensation in the sales gas pipeline based on one or more operational parameters of the sales gas pipeline and the one or both of the amount of glycol carryover and the amount of water carryover; and determining, by operation of the data processing apparatus, an amount of black powder formation of the sales gas based on the amount of glycol and water co-condensation.

In some implementations, the one or more operational parameters of the glycol dehydration unit include one or more of: a flowrate of wet gas that is input into the glycol dehydration unit, temperature of the wet gas that is input into the glycol dehydration unit, glycol circulation rate, or contactor pressure.

In some implementations, the one or more operational parameters of the glycol dehydration unit include one or more operational parameters of the glycol dehydration unit that are measured over time.

In some implementations, the one or more operational parameters of a sales gas pipeline include one or more of pressure or temperature of the sales gas pipeline or ambient temperature.

In some implementations, determining the one or both of the amount of glycol carryover and the amount of water carryover includes determining the amount of glycol carryover based on a model of glycol carryover, the model of glycol carryover including a function of the one or more operational parameters of the glycol dehydration unit, the model of glycol carryover matching at least one operating condition of the glycol dehydration unit.

In some implementations, determining the one or both of the amount of glycol carryover and the amount of water carryover includes determining the amount of water carryover based on a model of water carryover, the model of water carryover including a function of the one or more operational parameters of the glycol dehydration unit, the model of water carryover matching at least one operating condition of the glycol dehydration unit.

In some implementations, determining the one or both of the amount of glycol carryover and the amount of water carryover includes determining the amount of glycol carryover; determining the amount of water carryover; and confirming that the amount of water carryover is sufficient to co-condense with glycol in the sales gas in the sales gas pipeline.

In some implementations, determining the amount of glycol and water co-condensation in the sales gas pipeline includes determining the amount of glycol and water co-condensation in the sales gas pipeline on a model of the glycol and water co-condensation, the model of the glycol and water co-condensation including a function of the one or more operational parameters of the sales gas pipeline.

In some implementations, determining the amount of black powder formation of the sales gas includes determining the amount of black powder formation of the sales gas based on a model of black powder formation of the sales gas pipeline as a function of the amount of glycol and water co-condensation, the model of black powder formation matching at least one measurement of the black powder formation of the sales gas.

In some implementations, the method further includes performing maintenance of a filter station downstream to the sales gas pipeline and configured to filter black powder formation of the sales gas based on the amount of black powder formation of the sales gas.

In some aspects, a method for modeling black powder formation in a sales gas pipeline includes receiving, by operation of data processing apparatus, at least one measurement of black powder formation at a filter station downstream to a sales gas pipeline that receives sales gas output from a glycol dehydration unit in a gas plant; and generating, by operation of the data processing apparatus, a model of black powder formation of the sales gas as a function of an amount of glycol and water co-condensation in the sales gas according to a mathematical regression method or a statistical algorithm, the model of black powder formation matching the at least one measurement of black powder formation of the sales gas.

While certain aspects of the subject matter are generally described as computer-implemented software embodied on tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the description below. Other features and advantages of the disclosure will be apparent from the description and drawings, and from the claims.

BRIEF DESCRIPTION OF THE DRAWINGS

Like reference numbers and designations in the various drawings indicate like elements.

DETAILED DESCRIPTION

This disclosure describes systems and methods for evaluating black powder formation of hydrocarbon gas flowed through pipelines, such as, sales gas flowed through sales gas transmission pipelines. Example techniques are disclosed for computer-implemented modeling and computer-implemented predicting black powder formation of sales gas transmitted in gas pipelines.

In a sales gas system, one or more sales gas pipelines are at the downstream of a sales gas dehydration unit in a gas plant. Dehydrated sales gas output from the sales gas dehydration unit flows into the gas pipeline for transmission to customers. Although little or no water condensation (that is, moisture condensation) is assumed to be present if the water content in the sales gas is below a certain sales gas specification, black powder can be formed in the gas pipeline in practice due to pipeline corrosion, as a result of condensed water. The example techniques evaluate black powder formation of the sales gas in the gas pipeline, for example, by determining an amount of black powder formed in the gas pipeline based on a black powder formation model.

At a high level, the black powder formation model can receive various operating conditions of the sales gas dehydration unit and the sales gas pipeline as input variables, and return the amount of black powder formed in the gas pipeline as an output. For example, the amount of black powder formed in the gas pipeline is modeled as a function of operational parameters of a glycol de-hydration unit (for example, wet sweet feed gas flowrate and temperature, glycol circulation rate, and contactor pressure) and sales gas pipeline information (for example, sales gas pipeline temperature and pressure, and ambient temperature). Based on the black powder formation model, for given glycol de-hydration unit operational parameters and sales gas pipeline information, a corresponding amount of black powder formed in the gas pipeline can be predicted.

In some implementations, for improved prediction accuracy of the black powder formation and better manageability, the overall black powder formation model can be further divided into multiple sub-models. As an example, the overall black powder formation model includes a glycol and moisture carryover model, a glycol and moisture co-condensation model, and a black powder formation model. By using the glycol and moisture carryover model and glycol and moisture co-condensation model, a more accurate estimation of the amount of water condensation can be obtained, giving rise to a more accurate estimation of the black powder formation.

In some implementations, a glycol and moisture carryover model can be generated, or otherwise developed, by a process simulation for the upstream glycol dehydration unit. A process model can be tuned to match at least one operating point of the glycol dehydration unit. The process model is then used to predict the glycol and moisture carryover (for example, in terms of an amount of glycol carryover, an amount of water carryover, or both) in the sales gas at different operating conditions represented by different dehydration unit operation parameters. The dehydration unit operation parameters include sweet wet gas temperature and flowrate, lean glycol circulation rate, contactor pressure, etc. The simulation results are then used to develop a mathematical or statistical correlation model between the glycol and moisture carryover and the dehydration unit operation parameters, for example, based on curve fitting, regression, or other techniques. The mathematical or statistical correlation model is then used as the glycol and moisture carryover model to predict the glycol and moisture carryover based on the glycol unit operating conditions.

The glycol and moisture carryover can be presented, for example, by an amount of glycol carryover, an amount of water carryover, or both. In some implementations, both the amount of glycol carryover and the amount of water carryover are determined to make sure that the amount of water carryover is more than enough to co-condense with glycol in the sales gas pipeline.

In some implementations, moisture analyzers, such as online moisture analyzers or standalone moisture analyzers, can be used in the gas plant or gas pipeline. Maintaining accurate moisture readings can be difficult in practice. However, if there are reliable moisture analyzer readings, the readings can be used to derive a moisture carryover model. Additionally, they can provide supplemental accuracy check and enhancement for the moisture carryover modeling, based on the abovementioned process simulation. The process model has to match at least one operating condition of the glycol dehydration unit. Therefore, in a way, an accurate moisture reading is a continuous validation of the process model for moisture carryover. In some implementations, the moisture carryover model can be developed based on the process simulation or based on moisture readings from a moisture analyzer. In some implementations, the accurate moisture reading can be used to update, fine tune, or otherwise improve the moisture carryover model developed based on the process simulation.

In some implementations, a glycol and water co-condensation model can be obtained by another process simulation. The glycol and water co-condensation model can predict an amount of glycol and water co-condensation in the sales gas pipeline, taking into consideration the pipeline operating temperature and pressure, since glycol-water co-condensation is directly influenced by the sales gas temperature and pressure. In some implementations, the ambient temperature of the sales gas pipeline is also included in the glycol and water co-condensation model. The amount of glycol and water co-condensation can represent an amount of co-condensed glycol and water in the sales gas pipeline. In some implementations, the amount of glycol and water co-condensation in the sales gas pipeline can be represented by, for example, an amount of condensed glycol in the sales gas pipeline in the presence of condensed water, an amount of condensed water in the sales gas pipeline in the presence of condensed glycol, or both. The determined amount of co-condensed glycol and water can be added mathematically as the glycol and water accumulation over time. In some implementations, the starting point for calculating the glycol and water accumulation can be at the time just after pipeline scraping.

The black powder formation model can be developed, for example, to correlate an amount of black powder formed in the sales gas pipelines with an amount of glycol and water co-condensation in the sales gas pipelines. For example, the black powder formation model can be developed based on an amount of condensed glycol in the sales gas pipeline, an amount of condensed water in the sales gas pipeline, or both. In some implementations, using either the amount of condensed glycol or the amount of condensed water in the sales gas pipeline as an individual input variable of the black powder formation model is sufficient to give good modeling results. In some implementations, both the amount of condensed glycol and the amount of condensed water in the sales gas pipeline can be used as the input variables of the black powder formation model. The black powder formation model can be developed to match at least one black powder collection data point. The black powder formation model can be developed, for example, according to a statistical, regression, or another algorithm.

Based on the glycol and moisture carryover model, the glycol and moisture co-condensation model, and the black powder formation model, an amount of black powder formation in the sales gas pipeline can be predicted given an operating condition of the glycol dehydration unit and the sales gas pipelines information.

Example techniques are described in this disclosure that can automatically predict the black powder formation in the sales gas pipeline. The example techniques can help avoid blockage of the sales gas pipeline. The example techniques can help reduce or eliminate damages to compressors, filters and user equipment. The example techniques can provide better maintenance and extend the life span of a sales gas system. The example techniques can be used to show real time black powder formation in the pipeline, for example, by using black powder monitoring dashboard or other user interface, and hence provide black powder formation real time monitoring capability.

Figure 1:
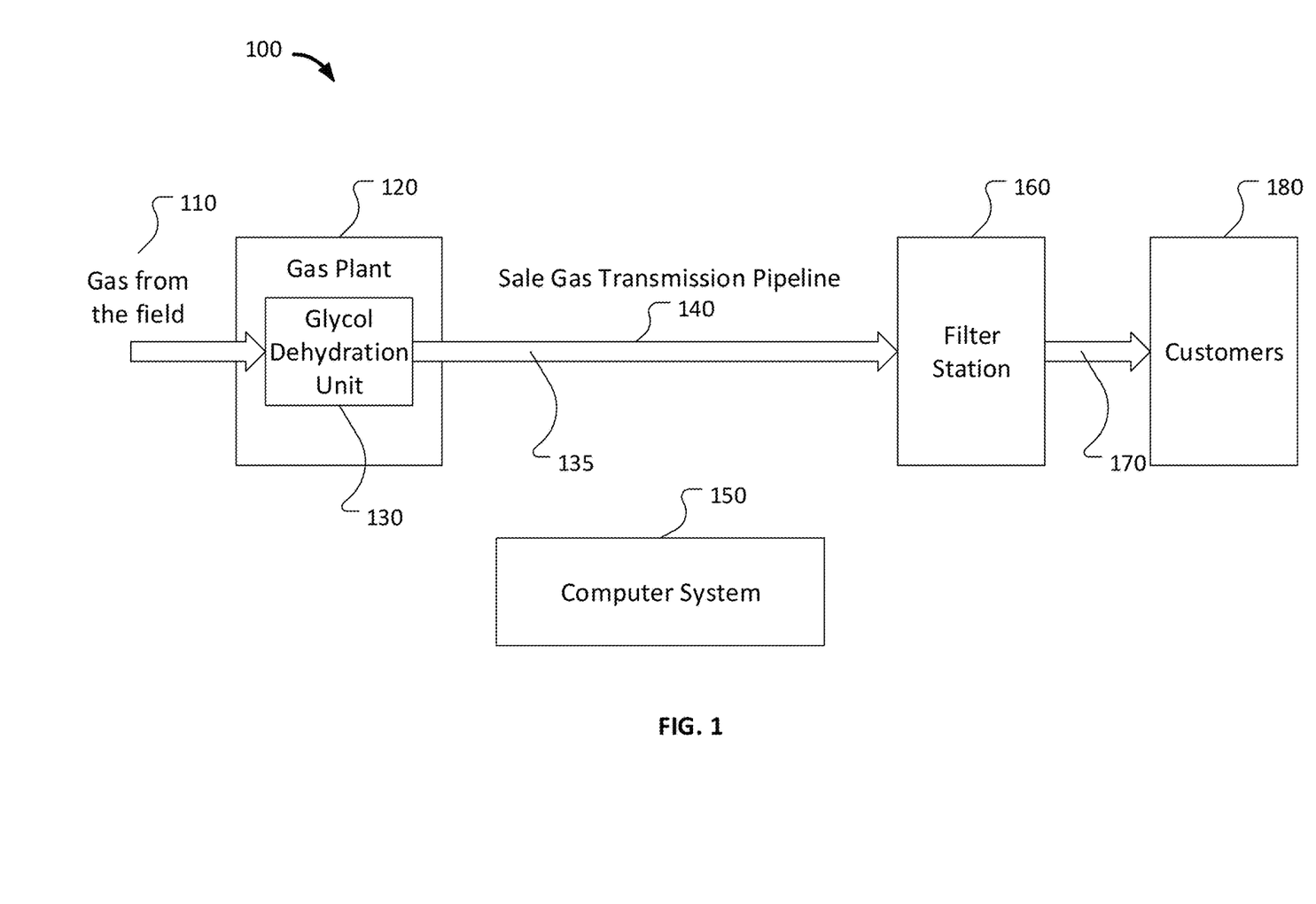
FIG. 1 is a diagram showing a schematic of an example sales gas system.

FIG. 1 is a diagram showing an example sales gas system 100. The sales gas system 100 can receive gas 110 (for example, wet sweet feed gas) from a gas field and output dehydrated sales gas 170 that meets certain specification (for example, in term of the moisture content) to customers 180. The sales gas system 100 includes, for example, a gas plant 120, a sales gas pipeline 140, and a filter station 160. The sales gas system 100 can further include a computer system 150, for example, for evaluating black powder formation of sales gas. For example, the computer system 150 is configured to model and predict black powder formation of sales gas 135 transmitted in the sales gas pipelines 140. The sales gas system 100 can include additional or different components and may be configured in a different manner from the example configuration shown in FIG. 1.

In some implementations, the gas plant 120 can be a natural gas processing plant. As shown in FIG. 1, the gas plant 120 has one or more glycol dehydration units 130 to remove excess water in the sales gas so that the sales gas meets the moisture specification. In some implementations, the sales gas system 100 can include multiple sales gas pipelines 140 at the downstream to the gas plant 120. The dehydrated sales gas 135 output from the glycol dehydration units 130 is flown into one or more sales gas pipelines 140 for transfer to the customers 180.

In some implementations, the glycol dehydration unit 130 can be a glycol dehydration unit that dehydrates the natural gas using glycol (for example, triethylene glycol (TEG) or other glycol). In some implementations, there are glycol and moisture carryovers in the sales gas 135 that is output from the glycol dehydration unit 130. In some implementations, once glycol is carried over with moisture in the sales gas pipeline 140, they co-condense in the sales gas pipeline 140 even when the sales gas meets the moisture specification. The co-condensed liquid solution can cover the surface of the sales gas pipeline 140, causing corrosion of the sales gas pipeline 140, and hence causing the formation of black powder in the sales gas pipeline 140.

In some implementations, one or more filter stations 160 are installed at the end of the one or more gas pipelines 140 before the sales gas is transferred to the customers 180. The filter station 160 filters and collects black powder particles of the dehydrated sales gas 135 flowing in the sales gas pipelines 140, for example, during a same period of time as the glycol co-condensed with water in the pipeline. The filtered sales gas 170 downstream to the filter station 160 is sent to the customers. In some implementations, the filter station 160 can be a solid particle filter station. For example, the filter station 160 can include two black powder filters, with one being online while the other being cleaned and made standby. When a filter has to be taken offline because enough black powder has been collected, the total amount of collected black powder can be weighed. The total amount can be used for computer-implemented model fitting and computer-implemented prediction of the black powder formation of the sales gas 135 transmitted in the sales gas pipelines 140.

In some implementations, the sales gas system 100 can further include one or more sensors (not shown) coupled to the gas plant 120. The one or more sensors can measure and monitor an operating condition of the glycol dehydration unit 130. In some implementations, the operating condition of the glycol dehydration unit 130 can be represented by the one or more operational parameters of the glycol dehydration unit 130. For example, the one or more operational parameters of the glycol dehydration unit 130 can include, but not limited to, one or more of a wet sweet feed gas flowrate, a wet sweet feed gas temperature, a glycol circulation rate, and a contactor pressure of the glycol dehydration unit 130. In some implementations, one or more operational parameters of the glycol dehydration unit 130 are obtained from glycol dehydration unit 130's plant operating data (for example, from an operation log or record). In some implementations, the one or more operational parameters of the glycol dehydration unit 130 are measured over time, for example, regularly, constantly, or from time to time. For example, the wet sweet feed gas flowrate and temperature can include daily or hourly average readings of a flowrate sensor and a temperature sensor of the wet sweet feed gas 110. In some implementations, the one or more operational parameters of the glycol dehydration unit 130 can be sent to the computer system 150 for storage and for evaluating black powder formation of the sales gas 135.

In some implementations, the sales gas system 100 can further include one or more sensors (not shown) coupled to the sales gas transmission pipeline 140. The one or more sensors can measure and monitor an operating condition of the sales gas transmission pipeline 140. In some implementations, the operating condition of the sales gas transmission pipeline 140 can be represented by one or more operational parameters of the sales gas transmission pipeline 140. For example, the one or more operational parameters of the sales gas transmission pipeline 140 can include one or more of internal pressure, temperature, or ambient temperature of the sales gas transmission pipeline 140. In some implementations, one or more operational parameters of the sales gas transmission pipeline 140 are obtained from operating data (for example, from an operation log or record) of the sales gas transmission pipeline 140. In some implementations, the one or more operational parameters of the sales gas transmission pipeline 140 are measured over time, for example, regularly, constantly, or from time to time. For example, the temperature and pressure of the sales gas transmission pipeline 140 can include daily or hourly average readings of a temperature sensor and a pressure sensor of the sales gas transmission pipeline 140. In some implementations, the one or more operational parameters of the sales gas transmission pipeline 140 be sent to the computer system 150 for storage and for evaluating black powder formation of the sales gas 135.

Figure 2:
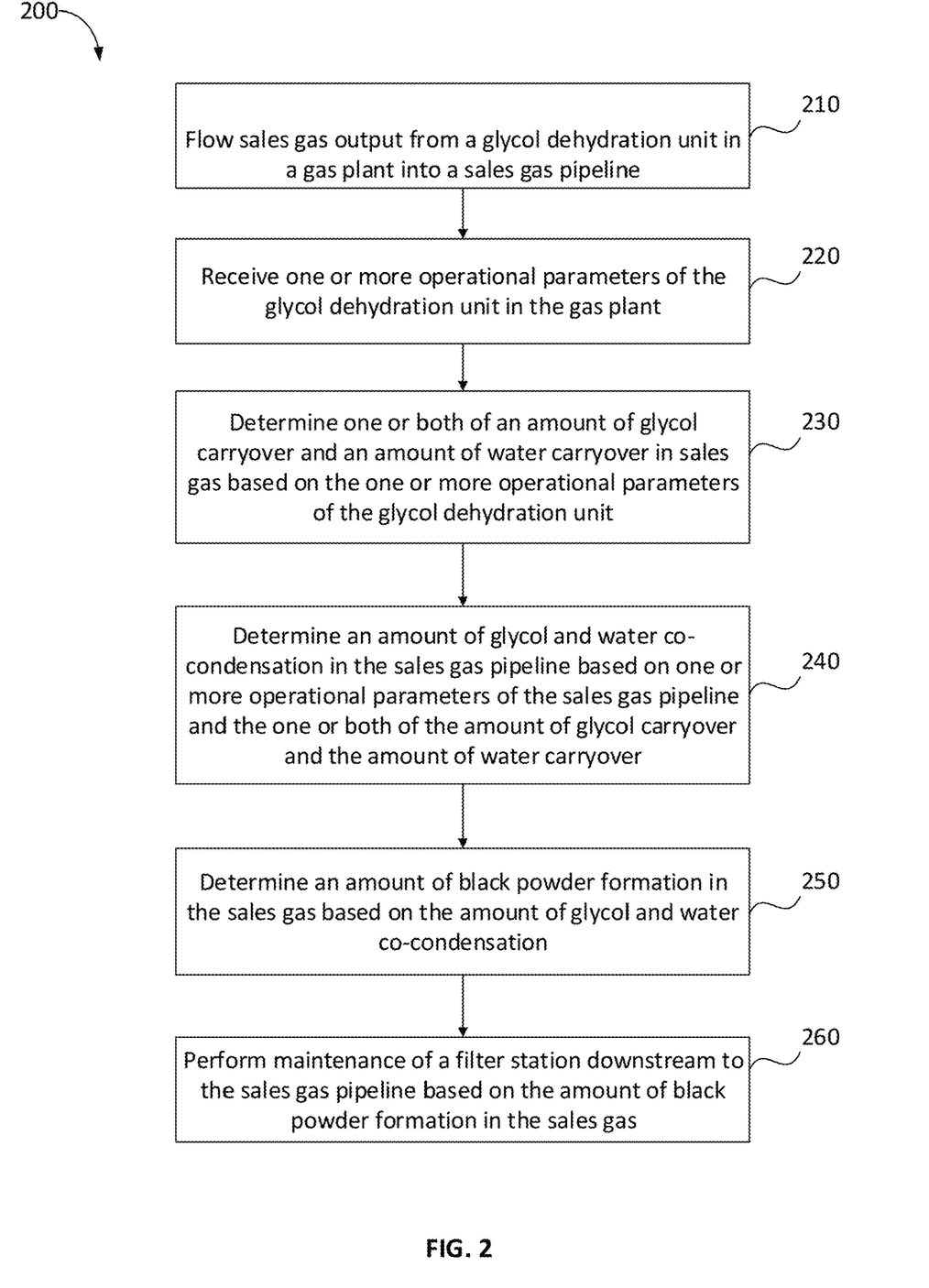
FIG. 2 is a flow chart showing an example method of evaluating black powder formation of sales gas in a sales gas pipeline.

FIG. 2 is a flow chart showing an example process 200 for evaluating black powder formation of sales gas, including modeling and predicting black powder formation of sales gas transmitted in gas pipelines. Some or all of the operations in the process 200 can be implemented, for example, by data processing apparatus (for example, the computer system 150 in or FIG. 1).

At 210, sales gas output from a glycol dehydration unit in a gas plant is flown into a sales gas pipeline. For example, the sales gas can be the sales gas 135 dehydrated by, and output from, the glycol dehydration unit 130 in the gas plant 120, then flown into the sales gas transmission pipeline 140 in FIG. 1.

At 220, one or more operational parameters of the glycol dehydration unit in the gas plant are received, for example, by data processing apparatus. In some implementations, the one or more operational parameters of the glycol dehydration unit can include one or more of a flowrate and temperature of gas (for example, wet sweet feed gas) input into the glycol dehydration unit, glycol circulation rate, contactor pressure, and other parameters. The one or more operational parameters of the glycol dehydration unit can be received, for example, from one or more sensors of the glycol dehydration unit (for example, regularly or in real time), an operation log or record of the glycol dehydration unit, or a data storage that stores historic operational parameters of the glycol dehydration unit.

At 230, one or both of an amount of glycol carryover and an amount of moisture carryover in sales gas output from the glycol dehydration unit are determined, for example, by the data processing apparatus, based on the one or more operational parameters of the glycol dehydration unit. In some implementations, the amount of glycol carryover and the amount moisture carryover in sales gas output from the glycol dehydration unit can be determined according to a process model for the gas plant glycol dehydration unit. The process model can be developed using modeling packages to simulate operations of the glycol dehydration unit. The process model for the gas plant glycol dehydration unit can be generated, tuned, or otherwise developed to match at least one operating condition of the glycol dehydration unit. The process model for the gas plant glycol dehydration unit is then used to predict the glycol carryover, the moisture carryover, or both in the sales gas at different operating conditions. In particular, the ability to determine the glycol carryover and the moisture carryover in the sales gas at different operating conditions allow for more accurate modeling of glycol-water con-condensation at 240, rather than focusing on glycol-water equilibria a fixed value of water content in the sales gas.

In some implementations, the operating condition of the glycol dehydration unit can be represented by the one or more operational parameters of the glycol dehydration unit that were measured previously or are measured in real time. In some implementations, the process model for the gas plant glycol dehydration unit is a model generated based on historical measurements of the operating condition of the glycol dehydration unit. In some implementations, the process model for the gas plant glycol dehydration unit can be updated, tuned, or otherwise developed based on updated (for example, real-time) actual or simulated measurements of the operating condition of the glycol dehydration unit.

In some implementations, the process model for the gas plant glycol dehydration unit can include a model of the glycol carryover, a model of the moisture carryover of the glycol dehydration unit, or both. Accordingly, determining the one or both of the amount of glycol carryover and the amount moisture carryover in sales gas includes determining the amount of glycol carryover based on the model of glycol carryover, determining the amount of water carryover based on the model of water carryover, or both. In some implementations, determining one or both of the amount of glycol carryover and the amount of water carryover includes determining both of the amount of glycol carryover and the amount of water carryover to confirm that the amount of water carryover is sufficient to co-condense with glycol in the sales gas in the sales gas pipeline. Such a confirmation can be made, for example, based on a predetermined threshold, empirical analysis, or other techniques.

In some implementations, each of the model of the glycol carryover and the model of the moisture carryover can be a function of the one or more operational parameters of the glycol dehydration unit. For example, the model of the glycol carryover can represent a mathematical correlation between the glycol carryover and the one or more operation parameters of the glycol dehydration unit. The following cubit equation (1) is an example of the mathematical correlation, where F is the wet sweet feed gas flowrate, T is the wet sweet feed gas temperature, a, d, c, and d are different correlation parameters. The correlation parameters a, d, c, and d can be determined, for example, based on measurements of the operating condition of the glycol dehydration unit according to curve fitting or other techniques.

$$\text{Glycol carryover} = (a_3F^3 + b_3F^2 + c_3F + d_3)T^3 + (a_2F^3 + b_2F^2 + c_2F + d_2)T^2 + (a_1F^3 + b_1F^2 + c_1F + d_1)T + (a_0F^3 + b_0F^2 + c_0F + d_0) \quad (1)$$

The mathematical correlation model of the glycol carryover as shown in equation (1) can then be used to predict the glycol carryover in the sales gas based on the glycol dehydration units' (for example, daily or hourly) operating conditions.

Figure 3:
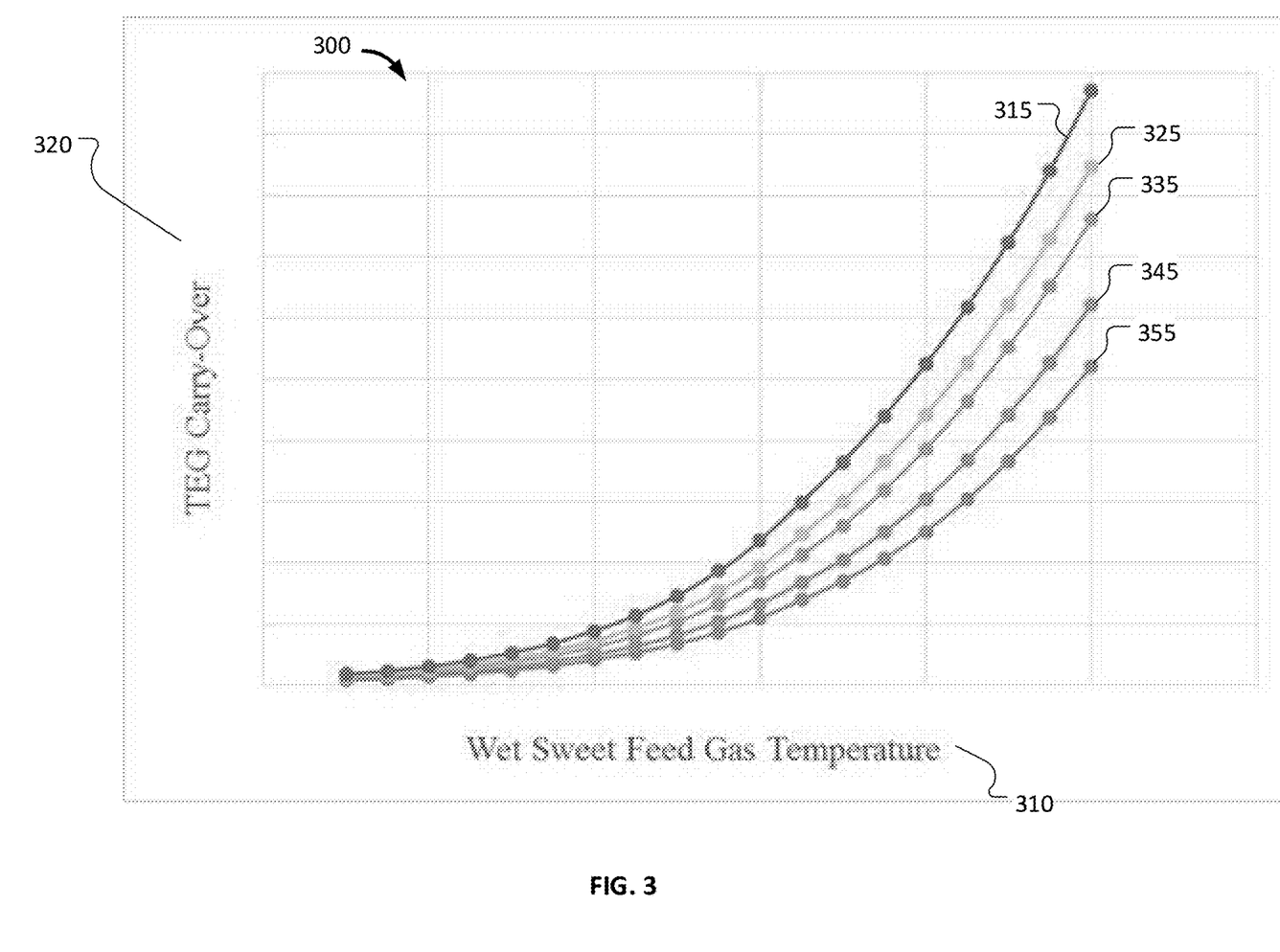
FIG. 3 is a plot showing an example model of glycol carryover in sales gas.

FIG. 3 is a plot 300 showing an example model of the glycol carryover in the sales gas. Specifically, the x-axis 310 represents wet sweet gas temperature; the x-axis 310 represents an amount of glycol carryover in the sales gas. Curves 315, 325, 335, 345, and 355 show the glycol carryovers in the sales gas for different wet sweet gas flowrates at different wet sweet gas temperatures.

Similarly, the mathematical correlation model for moisture carryover can be developed in a similar manner, given by equation (2).

$$\text{Water carryover} = (a_3F^3 + b_3F^2 + c_3F + d_3)T^3 + (a_2F^3 + b_2F^2 + c_2F + d_2)T^2 + (a_1F^3 + b_1F^2 + c_1F + d_1)T + (a_0F^3 + b_0F^2 + c_0F + d_0) \quad (2)$$

The mathematical correlation model of the moisture carryover as shown in equation (2) can then be used to predict the moisture carryover in the sales gas using the glycol dehydration unit's (for example, daily or hourly) operating conditions.

In some implementations, other types of functions can be used as the model of the glycol carryover and the model of the moisture carryover. For example, the model can include a multi-dimensional function (for example, a 3D surface) if additional parameters are taken into consideration. In some implementations, the model of the glycol carryover and the model of the moisture carryover can have different types of functions.

Referring back to 240, an amount of glycol and water co-condensation in the sales gas pipeline is determined, for example, by the data processing apparatus, based on one or more operational parameters of the sales gas pipeline, and the one or both of the amount of glycol carryover and the amount of moisture carryover. In some implementations, the one or more operational parameters of the sales gas pipeline include one or more operational parameters of the sales gas pipeline that are measured over time. In some implementations, the one or more operational parameters of the sales gas pipeline include, for example, one or more of temperature and pressure of the sales gas flowing in the sales gas pipeline, or ambient temperature of the sales gas pipeline.

The amount of glycol and water co-condensation can represent the amount of glycol and amount of water that are co-condensed in the sales gas pipeline. The amount of glycol and water co-condensation can be represented by an amount of condensed glycol (for example, in terms of volume or mass) in the sales gas pipeline in the presence of condensed water, a percentage of an amount of condensed glycol out of the amount of glycol carryover, an amount of condensed water (for example, in terms of volume or mass) in the sales gas pipeline in the presence of condensed glycol, a percentage of an amount of condensed water out of the amount of water carryover, or a combination of these and other metrics. The amount of glycol and water co-condensation can be time-dependent (for example, measured at certain time instants regularly, constantly, or from time to time) to reflect the amount of glycol and water co-condensation accumulated over a certain time period.

In some implementations, determining the amount of glycol and water co-condensation in the sales gas pipeline includes determining the amount of glycol and water co-condensation in the sales gas pipeline based on a model of the glycol and water co-condensation. The model of the glycol and water co-condensation can include a function of the one or more operational parameters of the sales gas pipeline. For example, a process simulation can be carried out to develop a mathematical correlation model of the glycol and water co-condensation as a function of the one or more operational parameters of the sales gas pipeline (for example, sales gas pipeline temperature and pressure).

In some implementations, the model of the glycol and water co-condensation can include a model for glycol condensation, a model for water condensation in the sales gas pipeline, or both. Each of the model for glycol condensation and the model for water condensation can be a function of the one or more operational parameters of the sales gas pipeline. For example, the model for the glycol condensation can include a mathematical correlation between an amount of the condensed glycol in the presence of condensed water in the sales gas pipeline and the operation parameters of the sales gas pipeline. For example, a second-order equation (3) can be derived to model the percentage of the amount of condensed glycol out of the amount of glycol carryover in the sales gas pipeline:

$$\% \text{ Glycol Condensation} = e*T^2 + f*T + g \qquad (3),$$

where T is sales gas temperature and e, f, and g are parametrical constants. The constants e, f, and g can be determined, for example, according to an empirical model, or developed based on historic or real-time measurements of the operating condition of the sales gas pipeline. For example, the constants e, f and, g can be determined according to curve fitting or other techniques based on collected data of the amount of condensed glycol and the amount of glycol and water co-condensation under different sales gas pipeline temperatures.

Figure 4:
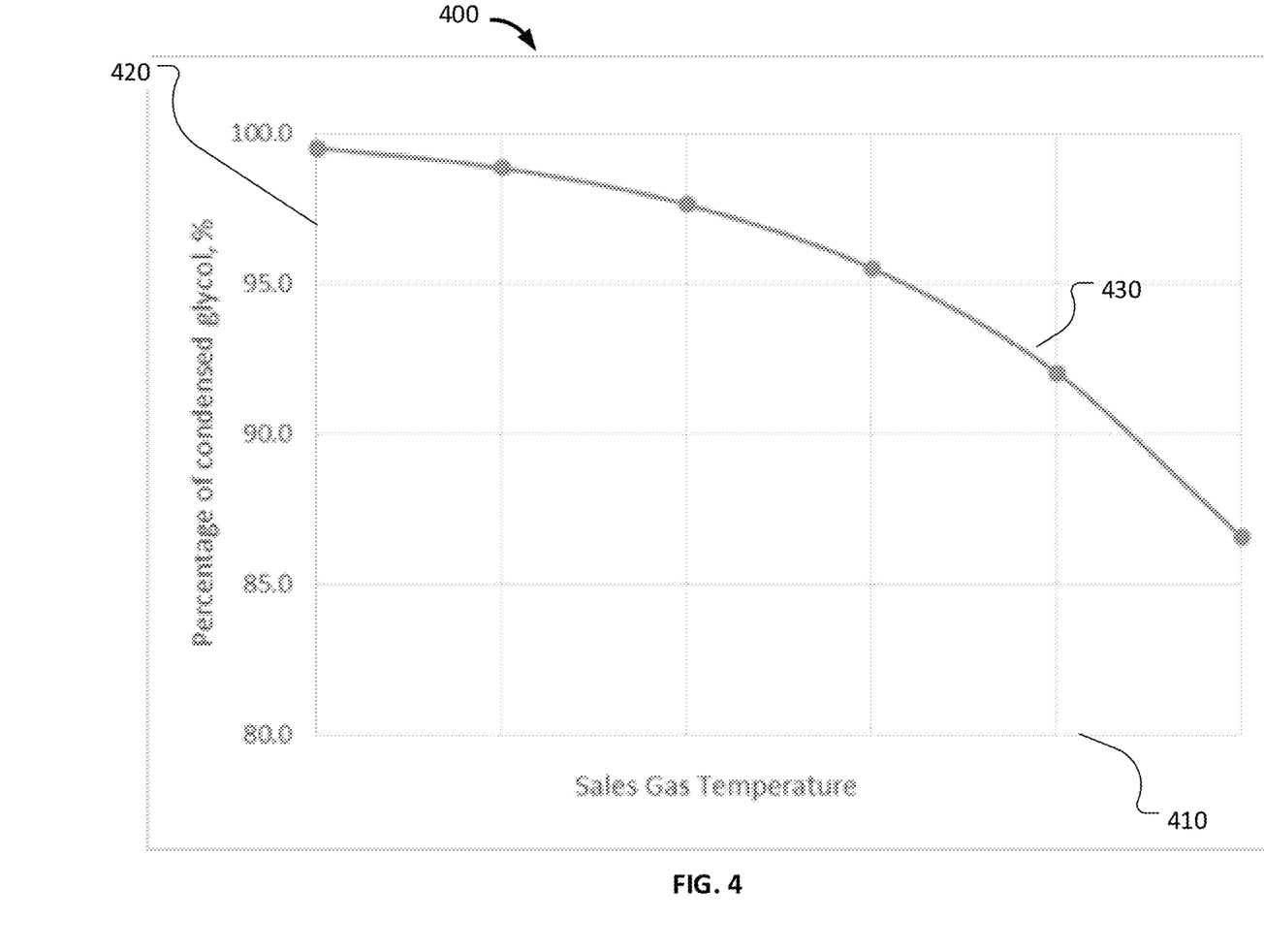
FIG. 4 is a plot showing an example model of glycol and water co-condensation in sales gas.

FIG. 4 is a plot showing an example model 400 of glycol and water co-condensation in sales gas. Specifically, the model 400 of glycol and water co-condensation is a model for glycol condensation in the presence of condensed water in the sales gas pipeline. The x-axis 410 represents sales gas temperature in the sales gas pipeline; the y-axis 420 represents a percentage of an amount of condensed glycol out of the amount of glycol carryover in the sales gas pipeline. The example model 400 of glycol and water co-condensation includes a curve 430 representing a correlation of a percentage of condensed glycol out of the glycol carryover in the sales gas pipeline as the sales gas temperature changes.

Similar, the model for water condensation in the presence of condensed glycol in the sales gas pipeline can be developed in a similar manner. In some implementations, functions other than the one shown in equation (3) can be used to model the relationship of the glycol and water co-condensation in the sales gas pipeline with respect to the operating condition (for example, the temperature and pressure) of the sales gas pipeline. In some implementations, the model of the glycol condensation and the model of the water condensation can have different types of functions.

In some implementations, determining the amount of glycol and water co-condensation in the sales gas pipeline includes determining a percentage of glycol condensation in the sales gas pipeline according to the model of glycol condensation; and determining the amount of glycol and water co-condensation in the sales gas based on the percentage of glycol condensation, the amount of glycol carryover, and the amount moisture carryover.

In this example, an amount of glycol carryover is determined according to the model for the glycol condensation (1) at 230; and the percentage of the carried-over glycol that is condensed is determined according to the model for the glycol condensation (3) at 240. Accordingly, the amount of condensed glycol can be determined by multiplying the determined amount of glycol carryover and the determined percentage of the condensed carried-over glycol. The amount of condensed water can also be determined in a similar or different manner. The amount of glycol condensation and the amount of water condensation can be added up together to determine the accumulation of condensed glycol and water in the sales gas pipeline. As such, the amount of glycol and water co-condensation in the sales gas pipeline is determined.

Referring back to 250, an amount of black powder formation of the sales gas is determined, for example, by the data processing apparatus, based on the amount of glycol and water co-condensation. In some implementations, the amount of black powder formation of the sales gas is determined based on a model of black powder formation. The model of black powder formation includes a function of an amount of glycol and water co-condensation. The model of black powder formation is developed to match at least one measurement of the black powder formation of the sales gas (for example, at least one black powder collection data point collected at a filter station). In some implementations, the model of black powder formation is built based on the assumption that black powder is formed uniformly in the pipeline once the inner surface area of the pipeline is covered by liquid glycol and water solution, and the more glycol and water co-condensation in the pipeline, the more inner surface area will be covered with black powder.

In some implementations, the model of black powder formation is developed to reflect the relationship between the amount of co-condensed glycol and water and the amount of black powder formed and collected during the same period of time. For example, a process simulation can be carried out to develop a mathematical correlation model between the amount of black powder formation and the amount of glycol and water co-condensation in the sales gas pipeline during the same period of time. For instance, the model of black powder formation can include a mathematical correlation model between the amount of black powder formation and the amount of condensed glycol, a mathematical correlation model between the amount of black powder formation and the amount of condensed water, or a mathematical correlation model between the amount of black powder formation and both the amount of condensed glycol and the amount of condensed water in the sales gas pipeline. The amount of black powder formation of the sales gas can be determined according to either of the above mathematical correlation models.

In some implementations, the model of black powder formation can include a statistical model developed according to k-nearest neighbors (KNN), Chi-square Automatic Interaction Detector (CHAID), Classification and Regression (C&R) Tree, or other algorithms. In some implementations, the model of black powder formation can include a mathematical regression model, including but not limited to linear regression model, developed according to mathematical regression algorithms. Typically, a mathematical regression model is parametric, that is, including one or more parameters (for example, constants) that define the mathematical regression model (for example, through curve fitting or regression). A statistical model does not necessarily need explicit parameters. In some implementations, a statistical model can be more accurate in predicting the amount of black powder formation. Additional or different models can be used as the model of black powder formation to match at least one measurement of the black powder formation of the sales gas, at the filter station, and to represent the correlation between the amount of black powder formation and the amount of glycol and water co-condensation in the sales gas pipeline.

Figure 5:
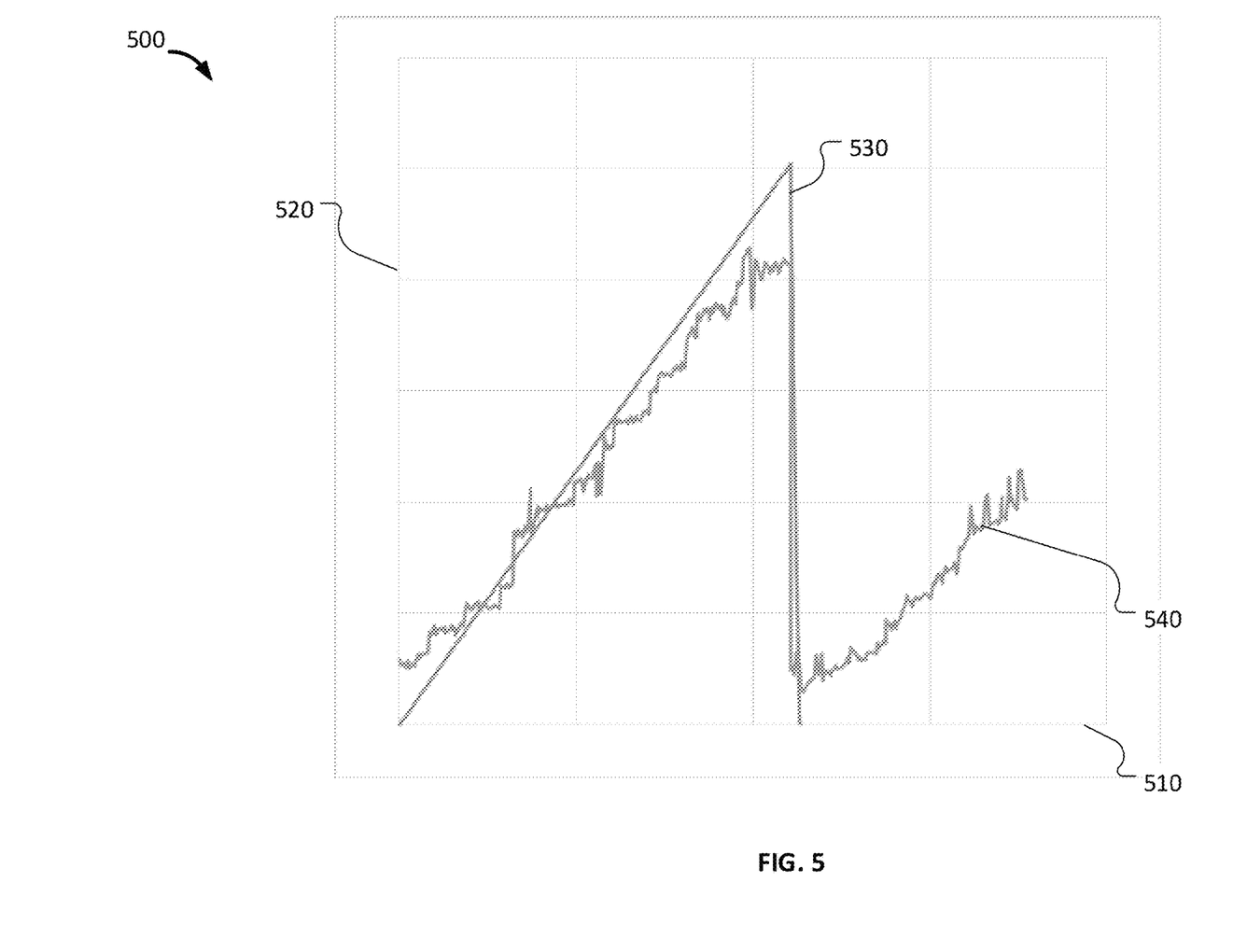
FIG. 5 is a plot showing an example model of black powder formation of sales gas.

FIG. 5 is a plot showing an example model 500 of black powder formation of sales gas. Specifically, the model 500 of black powder formation is a mathematical correlation model between the amount of black powder formation and the amount of condensed glycol in the presence of condensed water in the sales gas pipeline. As shown in FIG. 5, the x-axis 510 represents the amount of condensed glycol in the sales gas pipeline. The y-axis 520 represents an amount of black powder formation in the sales gas pipeline. The curve 530 represents collected black powder formation data (for example, measurements collected by a filter station). In this example, the model 500 of black powder formation includes a curve 540 that represents the correlation between the amount of black powder formation in the sales gas pipeline and the amount of condensed glycol in the sales gas pipeline. The curve 540 is obtained by fitting the collected data points on the curve 530 using the Chi-square Automatic Interaction Detector (CHAID) algorithm. The curve 540 can then be used for predicting the black powder formation of the sales gas for a given amount of condensed glycol in the sales gas pipeline.

In some implementations, the measurements, calculations, or determinations at 220-250 can be conducted on a regular or constant basis. For example, the glycol carryover represents an average carryover in an hour. Accordingly, the corresponding black powder formation calculated based on the glycol carryover is the black powder formation accumulated over an hour. In some implementations, the measurements, calculations, or determinations can also be daily (which may make the models and determinations less accurate), by every minute (which makes the models and determinations more accurately at the cost of a higher computational load), or at any other time instances, for example, based on system requirements or user inputs.

Referring back to 260, maintenance of a filter station is performed based on the determined amount of black powder formation of the sales gas. The filter station (for example, the filter station 160 in FIG. 1) is downstream of the sales gas pipeline and configured to filter the black powder formation of the sales gas. Performing maintenance of the filter station includes changing or cleaning a filter of the filter station at a certain time, to remove the accumulated black powder, based on the determined amount of black powder formation of the sales gas.

Figure 6:
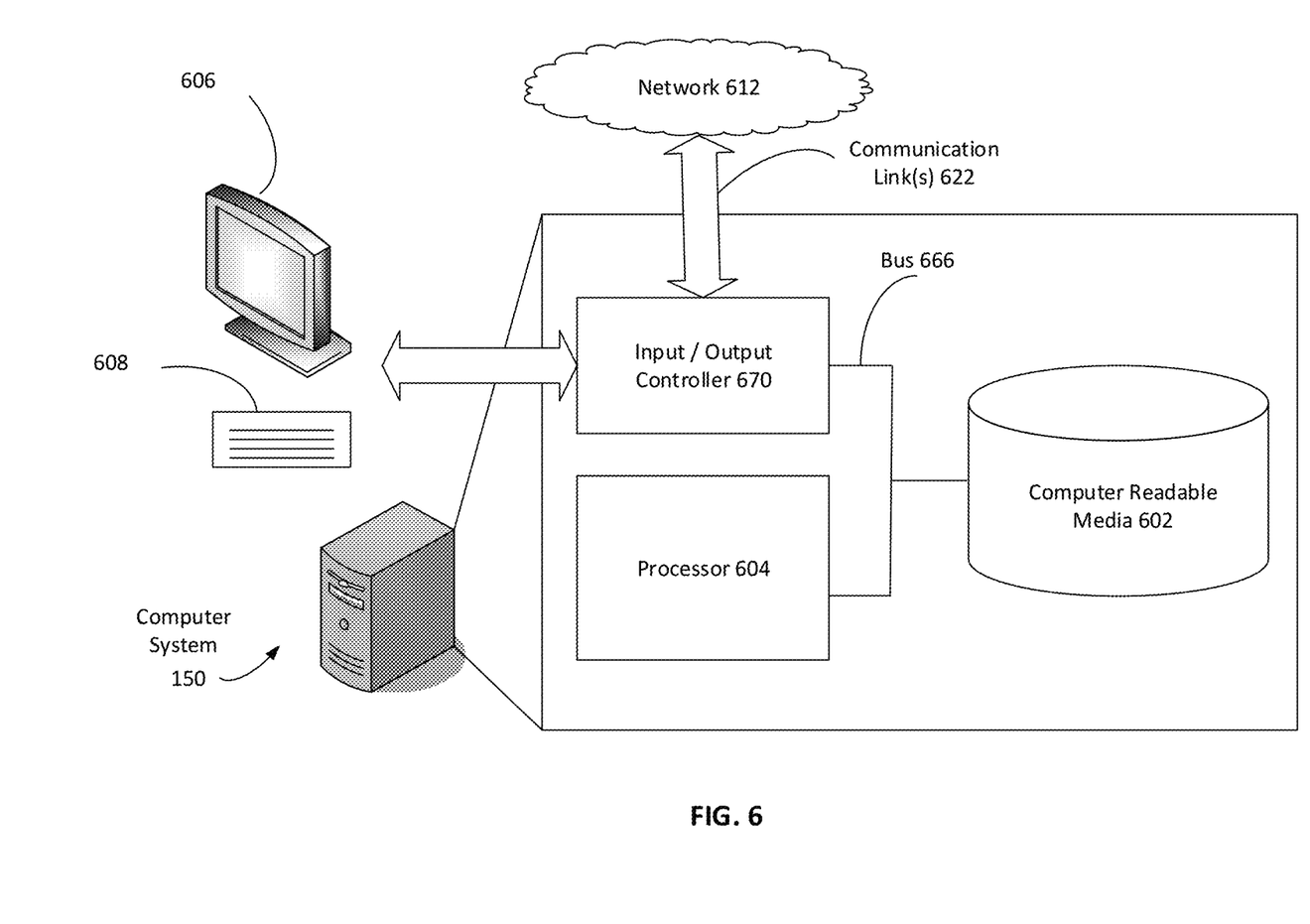
FIG. 6 is a diagram of an example configuration of the computer system in FIG. 1 for evaluating black powder formation of sales gas in a sales gas pipeline.

FIG. 6 is a diagram of an example configuration 600 of the computer system 150 in FIG. 1 for evaluating black powder formation of sales gas in a sales gas pipeline. The example computer system 150 can be located on site, within, or proximate to, the sales gas system 100, or at a remote location. In some implementations, the computer system 150 can be located at a data processing center, a computing facility, or another suitable location. The computer system 150 or any of its components can be located apart from the other components shown in FIG. 6. In some cases, all or part of the computer system 150 can be contained in a technical command center at the well site, in a real-time operations center at a remote location, in another appropriate location, or any suitable combination of these. The computer system 150 can include or access any suitable communication infrastructure (for example, communication link(s) 622 and network 612) for monitoring, accessing, and receiving data from and sending controlling signaling to the production wells and injection wells in the hydrocarbon field.

The example computer system 150 includes one or more of a data processing apparatus 604 (for example, one or more processors), a computer-readable medium 602 (for example, a memory), and input/output controllers 670 communicably coupled by a bus 666. The computer system 150 can perform one or more operations described with respect to FIGS. 1-5. For example, the computer system 150 can include processing apparatus and suitable computer-readable medium for evaluating black powder formation of sales gas, including modeling and predicting black powder formation of sales gas transmitted in gas pipelines. The computer system 150 can receive one or more operational parameters of a glycol dehydration unit in a gas plant, one or more operational parameters of the sales gas pipeline, and other data from one or more sensors of a sales gas system (for example, the sales gas system 100) or data storages (for example, the computer-readable medium 602 or another computer-readable medium of another device). The computer system 150 can generate, update, and execute one or more models (for example, a model of glycol carryover, a model of water carryover, a model of glycol and water co-condensation, and a model of black powder formation) for evaluating black powder formation of sales gas. The computer system 150 can determine an amount of glycol carryover and an amount moisture carryover in the sales gas, determine an amount of glycol and water co-condensation in the sales gas pipeline; and determine an amount of black powder formation of the sales gas. The computer system 150 can perform other operations as described with respect to FIGS. 1-5.

The computer-readable medium 602 can include, for example, a random access memory (RAM), a storage device (for example, a writable read-only memory (ROM) and/or others), a hard disk, and/or another type of storage medium. The computer system 150 can be preprogrammed and/or it can be programmed (and reprogrammed) by loading a program from another source (for example, from a CD-ROM, from another computer device through a data network, and/or in another manner). The input/output controller 670 is coupled to input/output devices (for example, the display device 606, input devices 608 (for example, keyboard, mouse, etc.), and/or other input/output devices) and to a network 612. The input/output devices receive and transmit data in analog or digital form over communication link(s) 622, such as a serial link, wireless link (for example, infrared, radio frequency, and/or others), parallel link, and/or another type of link.

The network 612 can include any type of data communication network. For example, the network 612 can include a wireless and/or a wired network, a Local Area Network (LAN), a Wide Area Network (WAN), a private network, a public network (such as the Internet), a WiFi network, a network that includes a satellite link, and/or another type of data communication network.

The operations described in this disclosure can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations of the foregoing. The apparatus can include special purpose logic circuitry, for example, a FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be deployed to be executed on one computer or on multiple computers that are located at one site or distributed across multiple sites and interconnected by a communication network.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together, in a single software product, or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system comprising:
a sales gas pipeline coupled to a glycol dehydration unit in a gas plant and operable to receive sales gas output from the gas plant; and
a computer system operable to:
receive one or more operational parameters of the glycol dehydration unit in the gas plant;
determine an amount of glycol carryover and an amount of water carryover in the sales gas output from the glycol dehydration unit, based on the one or more operational parameters of the glycol dehydration unit;
determine an amount of glycol and water co-condensation in the sales gas pipeline based on the amount of glycol carryover, the amount of water carryover, and one or more operational parameters of the sales gas pipeline; and
determine an amount of black powder formation of the sales gas in the sales gas pipeline based on the amount of glycol and water co-condensation.

2. The system of claim 1, further comprising the gas plant that comprises the glycol dehydration unit.

3. The system of claim 1, further comprising one or more sensors for measuring the one or more operational parameters of the glycol dehydration unit, wherein the one or more operational parameters of the glycol dehydration unit comprise one or more of: a flowrate of wet gas that is input into the glycol dehydration unit, temperature of the of wet gas that is input into the glycol dehydration unit, glycol circulation rate, or contactor pressure.

4. The system of claim 1, wherein the one or more operational parameters of the glycol dehydration unit are measured over time; and the computer system is operable to receive one or more operational parameters of the glycol dehydration unit over the time.

5. The system of claim 1, further comprising one or more sensors for measuring the one or more operational parameters of the sales gas pipeline, wherein the one or more operational parameters of the sales gas pipeline comprise one or more of pressure or temperature of the sales gas pipeline or ambient temperature.

6. The system of claim 1, further comprising one or more sensors for measuring at least one operating condition of the glycol dehydration unit, wherein the computer system is operable to execute a model of glycol carryover as a function of the one or more operational parameters of the glycol dehydration unit, the model of glycol carryover matching the at least one operating condition of the glycol dehydration unit.

7. The system of claim 1, further comprising one or more sensors for measuring at least one operating condition of the glycol dehydration unit, wherein the computer system is operable to execute a model of water carryover as a function of the one or more operational parameters of the glycol dehydration unit, the model of water carryover matching at least one operating condition of the glycol dehydration unit.

8. The system of claim 1, wherein the computer system is operable to determine the amount of glycol and water co-condensation in the sales gas pipeline based on a model of the glycol and water co-condensation, the model of the glycol and water co-condensation comprising a function of the one or more operational parameters of the sales gas pipeline.

9. The system of claim 1, further comprising a filter station downstream to the sales gas pipeline and configured to filter black powder formation of the sales gas; wherein the computer system is operable to:
receive a measurement at the filter station of the black powder formation of the sales gas; and
determine the amount of black powder formation of the sales gas based on a model of black powder formation, the model of black powder formation comprising a function of the amount of glycol and water co-condensation, the model of black powder formation matching the measurement of the black powder formation of the sales gas at the filter station.

10. A method comprising:
flowing sales gas output from a glycol dehydration unit in a gas plant into a sales gas pipeline;
receiving, by operation of data processing apparatus, one or more operational parameters of the glycol dehydration unit in the gas plant;
determining, by operation of the data processing apparatus, one or both of an amount of glycol carryover and an amount of water carryover in sales gas output from the glycol dehydration unit in the gas plant based on the one or more operational parameters of the glycol dehydration unit;

determining, by operation of the data processing apparatus, an amount of glycol and water co-condensation in the sales gas pipeline based on one or more operational parameters of the sales gas pipeline and the one or both of the amount of glycol carryover and the amount of water carryover; and determining, by operation of the data processing apparatus, an amount of black powder formation of the sales gas based on the amount of glycol and water co-condensation.

11. The method of claim 10, wherein the one or more operational parameters of the glycol dehydration unit comprise one or more of: a flowrate of wet gas that is input into the glycol dehydration unit, temperature of the wet gas that is input into the glycol dehydration unit, glycol circulation rate, or contactor pressure.

12. The method of claim 10, wherein the one or more operational parameters of the glycol dehydration unit comprise one or more operational parameters of the glycol dehydration unit that are measured over time.

13. The method of claim 10, wherein the one or more operational parameters of a sales gas pipeline comprise one or more of pressure or temperature of the sales gas pipeline or ambient temperature.

14. The method of claim 10, wherein determining the one or both of the amount of glycol carryover and the amount of water carryover comprises determining the amount of glycol carryover based on a model of glycol carryover, the model of glycol carryover comprising a function of the one or more operational parameters of the glycol dehydration unit, the model of glycol carryover matching at least one operating condition of the glycol dehydration unit.

15. The method of claim 10, wherein determining the one or both of the amount of glycol carryover and the amount of water carryover comprises determining the amount of water carryover based on a model of water carryover, the model of water carryover comprising a function of the one or more operational parameters of the glycol dehydration unit, the model of water carryover matching at least one operating condition of the glycol dehydration unit.

16. The method of claim 10, wherein determining the one or both of the amount of glycol carryover and the amount of water carryover comprises:
    determining the amount of glycol carryover;
    determining the amount of water carryover; and
    confirming that the amount of water carryover is sufficient to co-condense with glycol in the sales gas in the sales gas pipeline.

17. The method of claim 10, wherein determining the amount of glycol and water co-condensation in the sales gas pipeline comprises determining the amount of glycol and water co-condensation in the sales gas pipeline on a model of the glycol and water co-condensation, the model of the glycol and water co-condensation comprising a function of the one or more operational parameters of the sales gas pipeline.

18. The method of claim 10, wherein determining the amount of black powder formation of the sales gas comprises determining the amount of black powder formation of the sales gas based on a model of black powder formation of the sales gas pipeline as a function of the amount of glycol and water co-condensation, the model of black powder formation matching at least one measurement of the black powder formation of the sales gas.

19. The method of claim 10, further comprising performing maintenance of a filter station downstream to the sales gas pipeline and configured to filter black powder formation of the sales gas based on the amount of black powder formation of the sales gas.

20. A method for modeling black powder formation in a sales gas pipeline, the method comprising:
    receiving, by operation of data processing apparatus, at least one measurement of black powder formation at a filter station downstream to a sales gas pipeline that receives sales gas output from a glycol dehydration unit in a gas plant; and
    generating, by operation of the data processing apparatus, a model of black powder formation of the sales gas as a function of an amount of glycol and water co-condensation in the sales gas according to a mathematical regression method or a statistical algorithm, the model of black powder formation matching the at least one measurement of black powder formation of the sales gas.

* * * * *

UNITED STATES PATENT AND TRADEMARK OFFICE
CERTIFICATE OF CORRECTION

PATENT NO. : 10,648,891 B2
APPLICATION NO. : 15/452321
DATED : May 12, 2020
INVENTOR(S) : Yufeng He and Rohit Patwardhan Page 1 of 1

It is certified that error appears in the above-identified patent and that said Letters Patent is hereby corrected as shown below:

In the Claims

In Column 16, Line 11, Claim 3, after "of the" delete "of"

Signed and Sealed this
Ninth Day of February, 2021

Drew Hirshfeld
*Performing the Functions and Duties of the
Under Secretary of Commerce for Intellectual Property and
Director of the United States Patent and Trademark Office*